United States Patent
Shinobu et al.

(10) Patent No.: US 10,126,268 B2
(45) Date of Patent: Nov. 13, 2018

(54) SENSING SENSOR

(71) Applicant: NIHON DEMPA KOGYO CO., LTD., Tokyo (JP)

(72) Inventors: Wakako Shinobu, Saitama (JP); Hiroyuki Kukita, Saitama (JP); Shunichi Wakamatsu, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 115 days.

(21) Appl. No.: 15/352,580

(22) Filed: Nov. 16, 2016

(65) Prior Publication Data
US 2017/0146490 A1 May 25, 2017

(30) Foreign Application Priority Data
Nov. 20, 2015 (JP) .................. 2015-227731

(51) Int. Cl.
| | | |
|---|---|---|
| *G01N 29/02* | (2006.01) | |
| *B01L 3/00* | (2006.01) | |
| *G01N 29/036* | (2006.01) | |
| *G01N 33/487* | (2006.01) | |
| *G01N 33/543* | (2006.01) | |
| *G01N 33/48* | (2006.01) | |

(52) U.S. Cl.
CPC ...... *G01N 29/036* (2013.01); *B01L 3/502715* (2013.01); *G01N 33/487* (2013.01); *G01N 33/54366* (2013.01); *B01L 2200/10* (2013.01); *B01L 2300/0636* (2013.01); *B01L 2300/0816* (2013.01); *B01L 2300/0887* (2013.01); *B01L 2300/12* (2013.01)

(58) Field of Classification Search
CPC ...... G01N 29/036; G01N 29/02; G01N 29/00; G01N 33/487; G01N 33/48; G01N 33/483; G01N 33/54366; G01N 33/543; G01N 33/53; G01N 33/50; B01L 3/502715; B01L 3/5027; B01L 3/502; B01L 3/50
USPC ............ 422/82.01, 68.1, 50; 73/64.53, 53.01
See application file for complete search history.

(56) References Cited

U.S. PATENT DOCUMENTS

| | | | | |
|---|---|---|---|---|
| 2010/0313636 | A1* | 12/2010 | Wakamatsu | ......... G01N 29/022 73/64.53 |
| 2014/0250985 | A1* | 9/2014 | Shinobu | ............... G01N 29/022 73/64.53 |

FOREIGN PATENT DOCUMENTS

| | | |
|---|---|---|
| JP | 2005147778 | 6/2005 |
| JP | 2009206792 | 9/2009 |

* cited by examiner

*Primary Examiner* — Christine T Mui
(74) *Attorney, Agent, or Firm* — JCIPRNET

(57) ABSTRACT

A sensing sensor includes a first vibrating region, a second vibrating region, an adsorbing film, a blocking layer, a wiring board, a channel forming member arranged to cover a region of the one surface side of the wiring board to form a channel. The adsorbing film is arranged such that the adsorbing film is located in a region including the central portion in the front-rear direction of the one vibrating region. Assuming that the front end portion of the vibrating region is P1, the front end portion of the adsorbing film is P2, and the central portion of the vibrating region is C, the front end portion of the adsorbing film P2 satisfies a relational expression expressed as follows: (a distance from C to P1)×0.4≤(a distance from P1 to P2)≤(a distance from C to P1)×0.8.

7 Claims, 14 Drawing Sheets

SENSING SENSOR

CROSS-REFERENCE TO RELATED APPLICATIONS

This application is based on and claims priority under 35 U.S.C. § 119 to Japanese Patent Application No. 2015-227731, filed on Nov. 20, 2015, the entire content of which is incorporated herein by reference.

TECHNICAL FIELD

This disclosure relates to a sensing sensor to sense a sensing object by using a piezoelectric resonator where its unique vibration frequency varies when the sensing object is adsorbed by an adsorption film arranged on the surface of the sensing sensor.

DESCRIPTION OF THE RELATED ART

As a sensing method of a sensing object in a sample fluid, for example, a trace amount of protein in blood or serum, there is disclosed a sensing sensor, for example, using a Quartz Crystal Microbalance (QCM) as disclosed in Japanese Unexamined Patent Application Publication No. 2009-206792. The QCM uses a crystal unit where an adsorption film adsorbing a sensing object by antigen-antibody reaction is arranged on a surface of an excitation electrode. The QCM grasps a load by the mass of the adsorbed sensing object in a sample solution as a frequency variation of the crystal unit, and thus the sensing object is quantitated. The use of the basic principle allows application to simple measurement employed for diagnosis in a medical front and food inspection.

In this case, the sensing sensor uses a microfluidic chip and foul's an extremely narrow reaction space in which the antigen-antibody reaction is conducted. The microfluidic chip is made of polydimethylsiloxane (PDMS). Placing a microfluidic chip on a dedicated QCM sensor creates a minute reaction portion. Since the use of the microfluidic chip allows considerable reduction in reaction capacity, the microfluidic chip passes through the surface of the electrode without diluting the sample. This has an advantage of high sensitivity for a low-concentration sample.

A crystal resonator has the largest amplitude in a central portion of a vibrating region. Consequently, vibration energy is largest in the central portion of the vibrating region, and the vibration energy tends to decrease with increase of distance from the central portion of the vibrating region.

Incidentally, when a sample solution with a sensing object is supplied to a supply channel, and the sensing object is adsorbed in an adsorption film, the upstream region of the supply channel more easily adsorbs the sensing object, of the region where the adsorption film is arranged. Thus, there is a problem that a sensing accuracy decreases as follows: in a sample solution with a low-concentration sensing object, the upstream region of the adsorption film adsorbs the sensing object, and thus the region with large vibration of the downstream side absorbs an insufficient amount of the sensing object.

Japanese Unexamined Patent Application Publication No. 2005-147778 disclose a technique that blocks adsorption of a sensing object in a portion other than an electrode by arranging a blocking layer in the portion other than the electrode of the crystal esonator. However, this does not solve the problem of this disclosure.

A need thus exists for a sensing sensor which is not susceptible to the drawback mentioned above.

SUMMARY

According to an aspect of this disclosure, there is provided a sensing sensor including a first vibrating region and a second vibrating region, an adsorbing film, a blocking layer, a wiring board, and a channel forming member. The first vibrating region and a second vibrating region are constituted with respective excitation electrodes arranged on one surface side and another surface side of a common crystal element. The first vibrating region and the second vibrating region are laterally separated with one another. The adsorbing film is formed on the surface of the excitation electrode in the one surface side corresponding to one vibrating region of the first vibrating region and the second vibrating region. The adsorbing film adsorbs a sensing object in a sample solution. The blocking layer is arranged over a whole region other than the region where the adsorbing film is formed on the excitation electrode in the one surface side. The blocking layer blocks adsorption of the sensing object in the sample solution. The wiring board includes a connection terminal portion to connect the excitation electrode to a frequency measuring unit. The crystal element is fixed to the wiring board such that the crystal element forms a space in the other surface side of the first vibrating region and the second vibrating region. The channel forming member is arranged to cover a region of the one surface side of the wiring board to form a channel that causes the sample solution to flow from a front end side toward a rear end side with the region, the region of the one surface side of the wiring board including the first vibrating region and the second vibrating region in the one surface side of the crystal element. The channel includes an injection port for injecting the sample solution in a front end side of the channel and a discharge port for discharging the sample solution from a rear end side of the channel. The adsorbing film is arranged such that the adsorbing film is located in a region including the central portion in the front-rear direction of the one vibrating region. Assuming that the front end portion of the vibrating region is P1, the front end portion of the adsorbing film is P2, and the central portion of the vibrating region is C, the front end portion of the adsorbing film P2 satisfies a relational expression expressed as follows: (a distance from C to P1)×0.4≤(a distance from P1 to P2)≤(a distance from C to P1)×0.8.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

A description will be given of a sensing device using a sensing sensor according to an embodiment disclosed here. The sensing device is constituted to detect presence/absence of an antigen such as a virus in a sample solution obtained, for example, from nasal cavity swab of a human, and to determine whether or not the human has been infected with the virus, by using a microfluidic chip. As illustrated in an external perspective view in FIG. 1, the sensing device includes a main body portion 12 and a sensing sensor 2. The sensing sensor 2 is removably connected to an insertion port 17 formed in the main body portion 12. A display unit 16 constituted with, for example, a liquid crystal display screen is arranged in the top surface of the main body portion 12. The display unit 16 displays, for example, an output frequency of an oscillator circuit, which will be described later, located inside the main body portion 12, a measurement result such as an amount of frequency variation, presence/absence of detection of the sensing object, or similar information.

Figure 1:
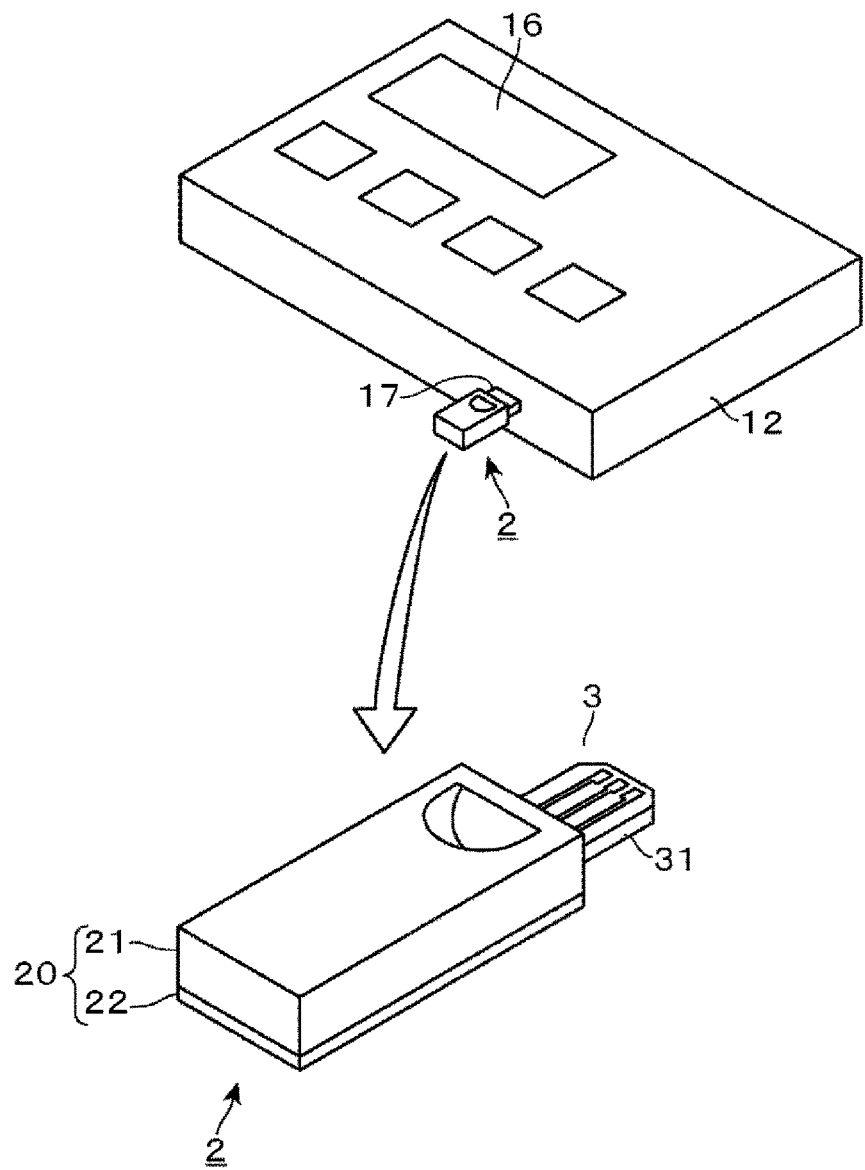
FIG. 1 is a perspective view of a sensing device and a sensing sensor according to this disclosure.
Figure 2:
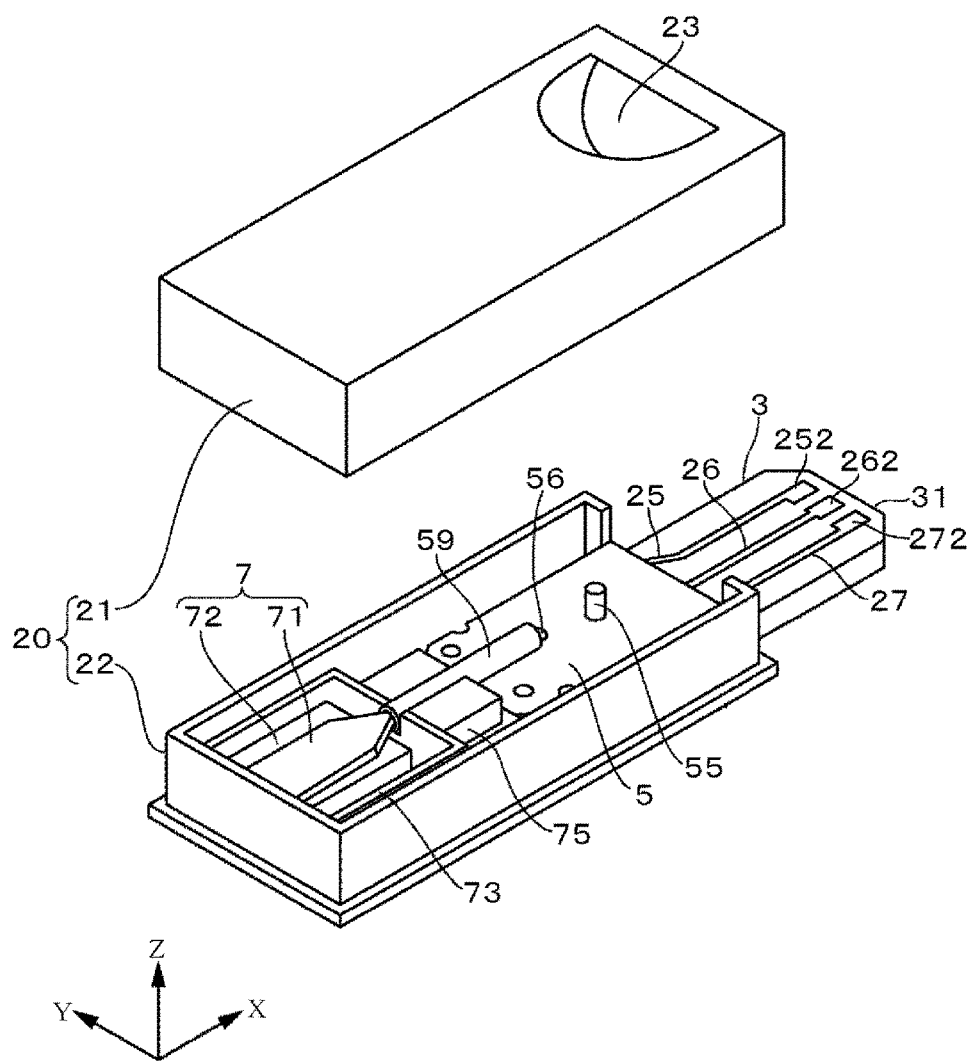
FIG. 2 is an exploded perspective view of the sensing sensor.
Figure 3:
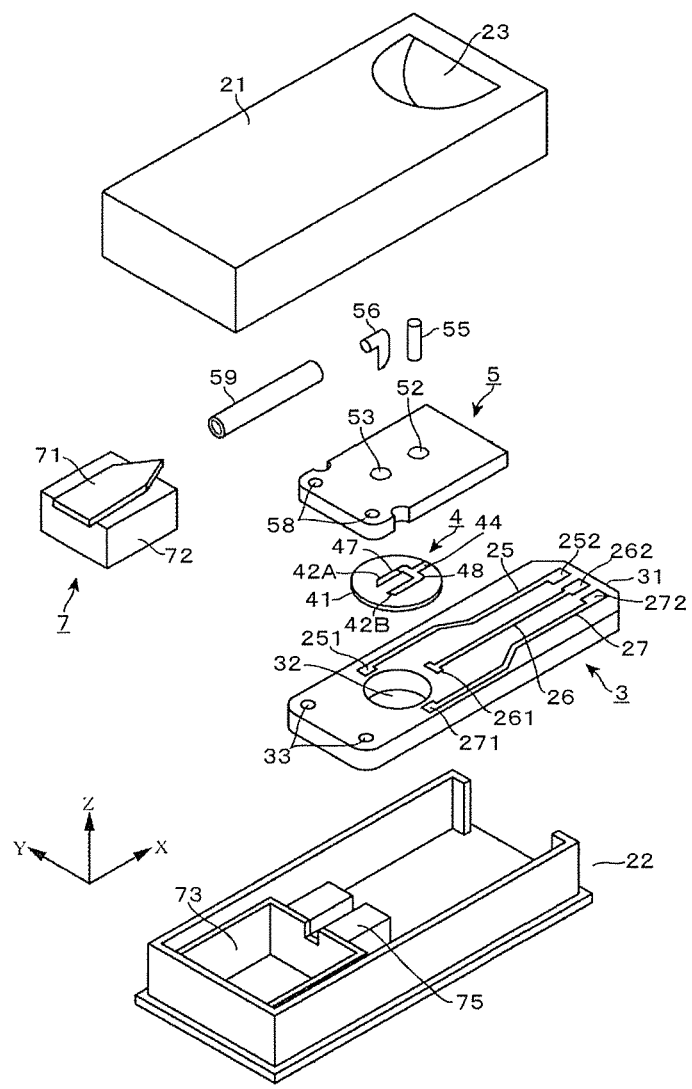
FIG. 3 is an exploded perspective view illustrating top surface side of respective members of the sensing sensor.
Figure 4:
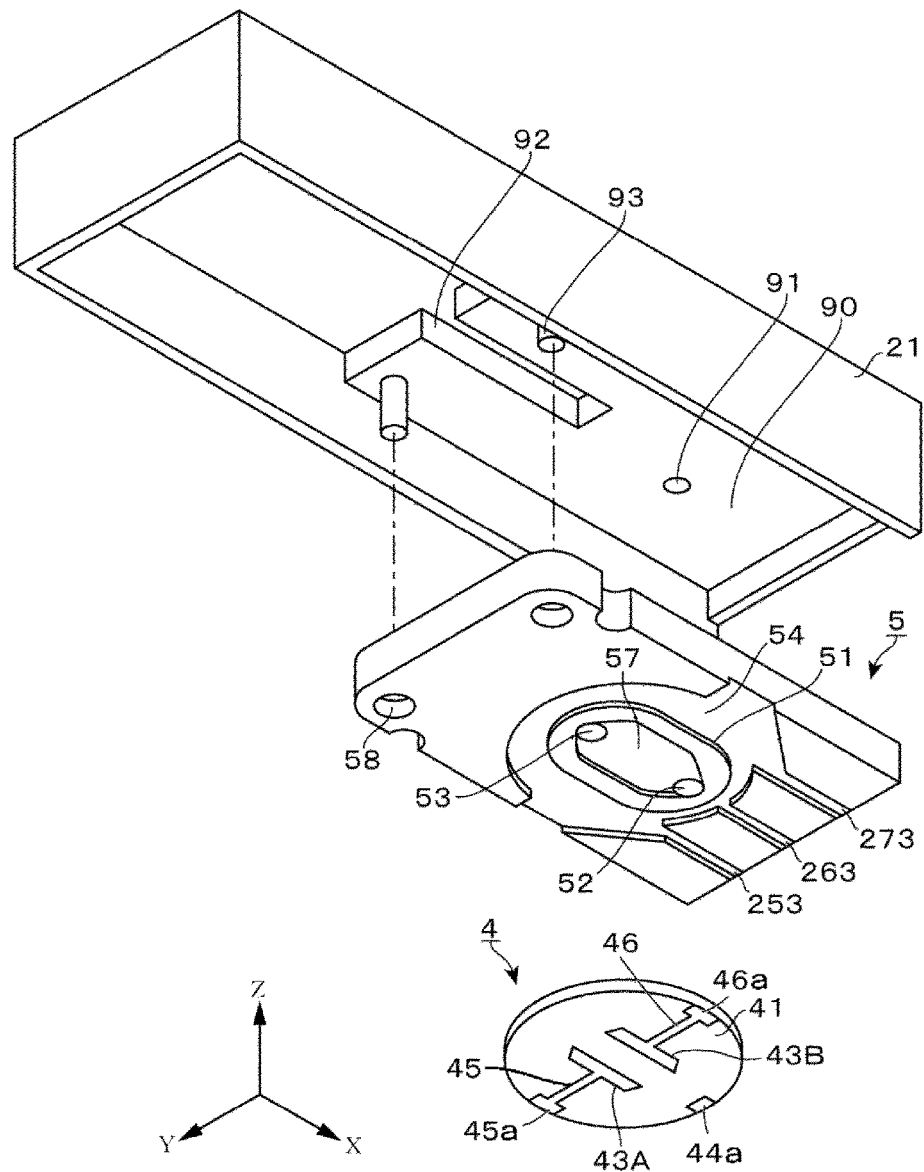
FIG. 4 is an exploded perspective view illustrating inferior surface sides of a part of the members of the sensing sensor.
Figure 5:
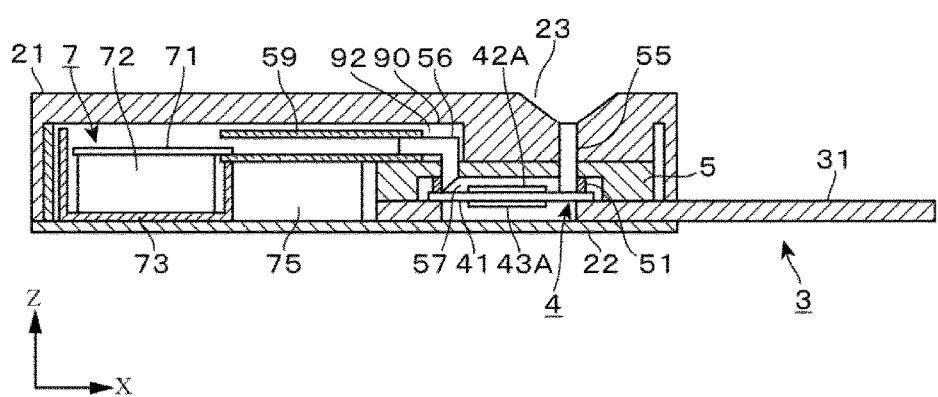
FIG. 5 is a longitudinal cross-sectional side view of the sensing sensor.

Subsequently, the sensing sensor 2 will be described. FIG. 2 is a perspective view illustrating a state where an upper-side cover body 21 in the sensing sensor 2 illustrated in FIG. 1 is removed. FIG. 3 and FIG. 4 are perspective views illustrating front surface sides (top surface side) of respective members and back surface sides (inferior surface sides) of a part of the members of the sensing sensor 2, respectively. FIG. 5 illustrates a longitudinal cross-sectional view of the sensing sensor 2.

The sensing sensor 2 includes a container 20 constituted of the upper-side cover body 21 and a lower-side case 22 as illustrated in FIG. 2. A wiring board 3 with a shape extended in a longitudinal direction as illustrated in FIG. 3 is arranged over the lower-side case 22, and an insertion portion 31 that is inserted into the above-described insertion port 17 of the main body portion 12 is formed at one end side of the longitudinal direction in the wiring board 3.

In the following description, the insertion portion 31 side of the sensing sensor 2 denotes the front, and the other end side denotes the rear.

At the position of the rear side of the wiring board 3, a through hole 32 is formed. The wiring board 3 is arranged such that the bottom surface of the lower-side case 22 covers the through hole 32, and the insertion portion 31 protrudes outside the lower-side case 22. The wiring board 3 includes three wirings 25 to 27 extending in the longitudinal direction on its front surface side. In the insertion portion 31, terminal portions 252, 262, and 272 are formed at the one end side of the respective wirings 25 to 27, respectively. In the outer edge of the through hole 32, terminal portions 251, 261 and 271 are formed in the other end side of the respective wirings 25 to 27, respectively. Further, in the further rear of the through hole 32 in the wiring board 3, two hole portions 33 for locating the horizontal position of the wiring board 3 are formed alongside in the width direction.

Figure 6A:
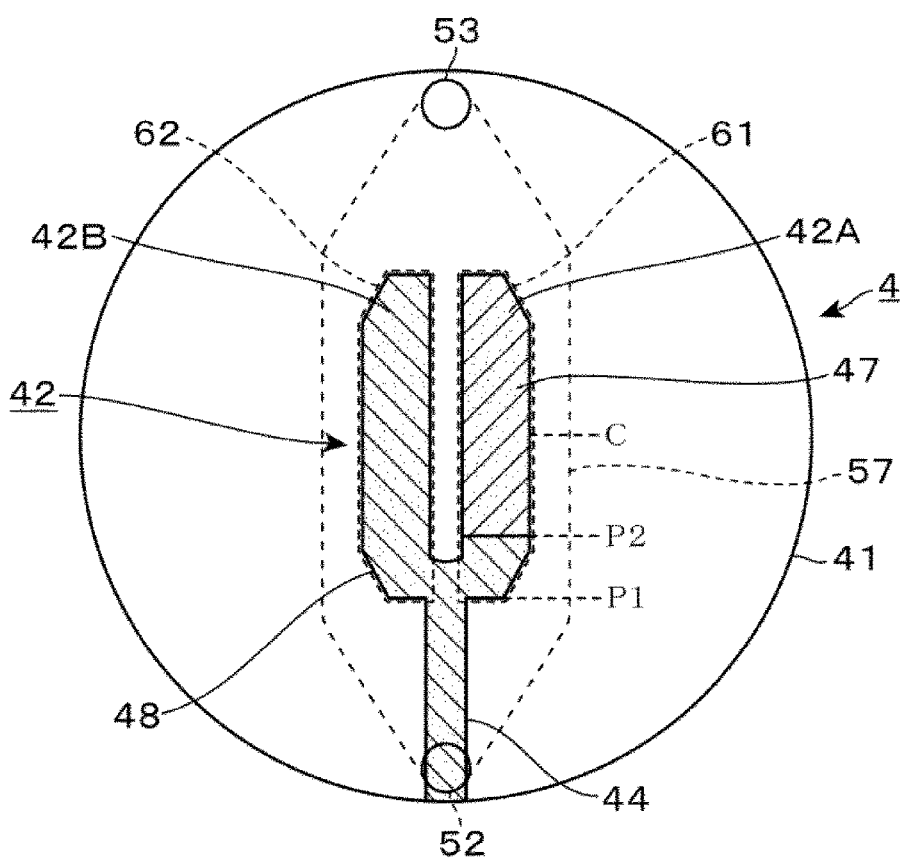
FIG. 6A is a plan view illustrating a front surface side of a crystal resonator.
Figure 6B:
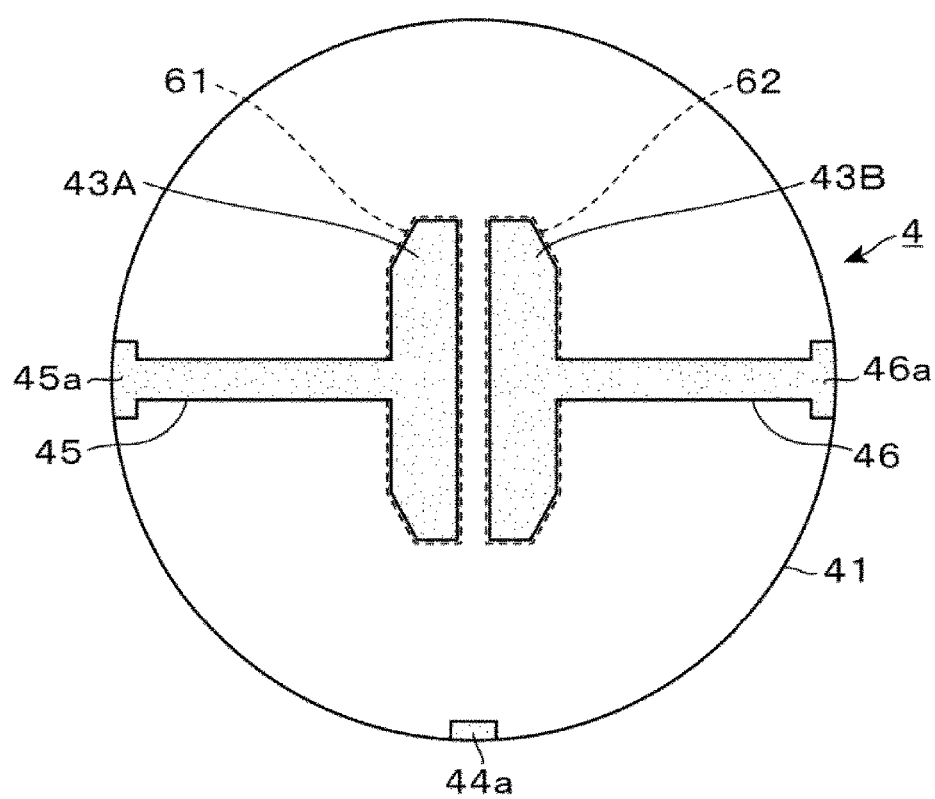
FIG. 6B is a plan view illustrating a back surface side of a crystal resonator.

Subsequently, a crystal resonator 4 will be described by referring to FIG. 6A and FIG. 6B illustrating its front surface side and back surface side, respectively. The crystal resonator 4 is configured with a circular-plate-shaped crystal element 41 constituted of, for example, AT-cut. In the back surface side of the crystal resonator 4, first and second excitation electrodes 43A and 43B made by, for example, gold (Au) extend in parallel with one another. In the front surface side of the crystal resonator 4, a tuning fork shaped common electrode 42 is arranged at the position facing with the first excitation electrode 43A and the second excitation electrode 43B. The common electrode 42 connects two excitation electrodes 42A and 42B that are made of, for example, gold (Au) and extend in parallel in a front side. The excitation electrode 42A in the common electrode 42 and the first excitation electrode 43A of the crystal resonator 4 sandwich a region to form a first vibrating region 61. The excitation electrode 42B and the second excitation electrode 43B sandwich a region to form a second vibrating region 62. These first and second vibrating regions 61 and 62 are separately arranged with one another and vibrate independently and respectively.

An extraction electrode 44 extends from the common electrode 42 toward the front-side peripheral edge portion of the crystal element 41, and further extends on the side surface of the crystal element 41 to form a terminal portion 44a at the peripheral edge portion of the back surface. Extraction electrodes 45 and 46 extend from the first and second excitation electrodes 43A and 43B toward the peripheral edge of the crystal element 41 to form terminal portions 45a and 46a at the peripheral edge portion of the crystal element 41, respectively.

An adsorbing film 47 that is constituted with antibody selectively combining with a sensing object is arranged in the region, which serves as the first vibrating region 61, on the surface of the one excitation electrode 42A in the common electrode 42. Further, in the common electrode 42, a blocking film 48 that inhibits adhesion of the sensing object is arranged in the region other than the region with the adsorbing film 47 and in the extraction electrode 44. The adsorbing film 47 and blocking film 48 will be described along with a forming method of these films.

Figure 7:
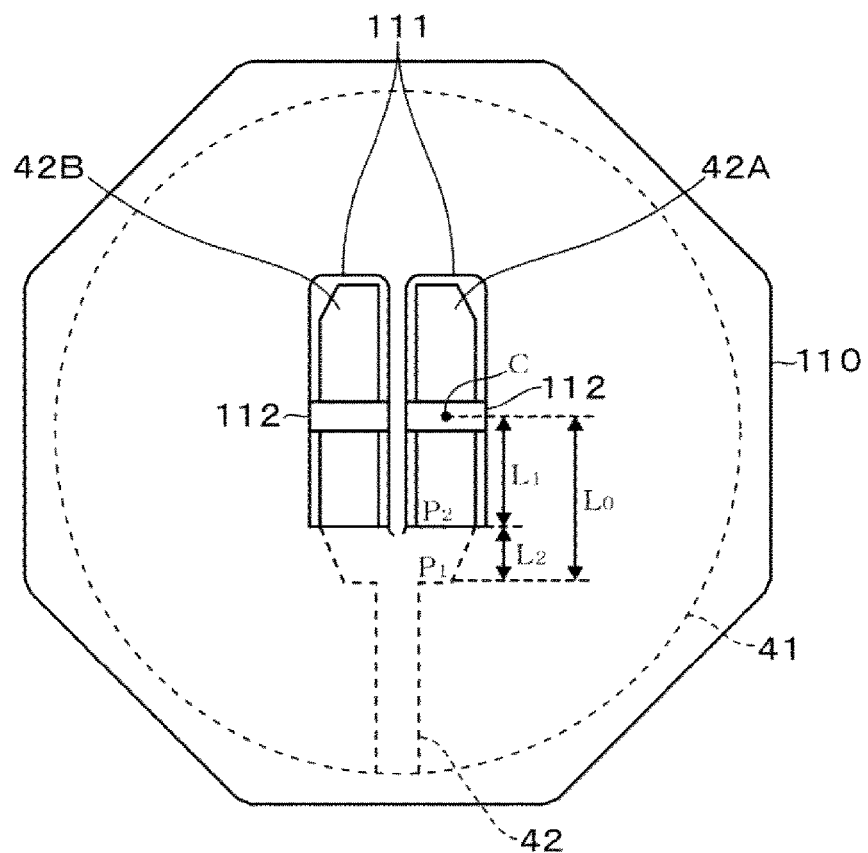
FIG. 7 is a plan view illustrating a rubber plate for arranging an adsorption film.

FIG. 7 illustrates a rubber plate 110 for arranging antibody. The rubber plate 110 is constituted in, for example, a substantially rectangular plate shape larger than the crystal element 41. The rubber plate 110 includes two slits 111 formed alongside in the width direction of the slits 111. Stacking the rubber plate 110 on the front surface side of the crystal element 41 causes the back surface side of the rubber plate 110 to closely contact the front surface of the crystal element 41. Then, each slit 111 faces the region that has a length of 80% with respect to the length of the first and second vibrating regions 61 and 62, from the rear-side end portion in the corresponding first and second vibrating regions 61 and 62, respectively. A supporting portion 112 is arranged in the center of each slit 111 in the width direction for preventing breakage of the slit 111. Placing the rubber plate 110 on the crystal element 41 forms gaps between the supporting portions 112 and the crystal element 41.

After the formation of the common electrode 42, the first and second excitation electrodes 43A and 43B, the extraction electrodes 44 to 46, and the terminal portions 44a to 46a to the crystal element 41, the rubber plate 110 is arranged such that the slits 111 are aligned with the regions that have a length of 80% with respect to the length of the first and second vibrating regions 61 and 62, from the rear-side end portion in the first and second vibrating regions 61 and 62.

Then, after fixation of the crystal element 41 and the rubber plate 110 by, for example, a tool, a solution containing antibody is injected in the slit 111 of the first vibrating region 61 side by an injector. Since the rubber plate 110 and the crystal element 41 are in close contact, the solution containing the antibody expands in the slit 111, and the antibody adheres on the surface of the common electrode 42 in the range that the slit 111 faces, namely, in the range that has a length of 80% of the length of the first vibrating region 61 from the rear-side end portion of the first vibrating region 61. Consequently, assuming that the central portion of the first vibrating region 61 is C, and the front-side end portion of the first vibrating region 61 is P1, then the front-side end portion P2 of the adsorbing film 47 is formed at the position expressed as follows: (a distance L0 from C to P1)×0.4=(a distance L2 from P1 to P2).

After removal of the tool and the rubber plate 110, applying a blocking agent, for example, such as Bovine Serum Albumin (BSA) or skim milk over the whole common electrode 42 on the front surface of the crystal element 41 forms the blocking film 48. At this time, because the antibody has already adhered, the blocking agent hardly adheres in the region of the adsorbing film 47 where the antibody has preliminarily been fixed. Consequently, the first vibrating region 61 in the common electrode 42 includes the blocking film 48 where the blocking agent has been applied in the region of the range within 20% of the length of the first vibrating region 61 from the front-side end portion of the first vibrating region 61. The first vibrating region 61 in the common electrode 42 includes the adsorbing film 47 where the antibody has been applied in the downstream-side region with respect to the position of the length L2, which is 20% of the length of the first vibrating region 61 from the front-side end portion.

The crystal resonator 4 is placed such that the first and second excitation electrodes 43A and 43B face the through hole 32 of the wiring board 3, and the terminal portions 44a to 46a overlap with the corresponding terminal portions 261, 251, and 271 arranged on the wiring board 3, respectively, and then is bonded with a conductive adhesive.

A channel forming member 5 is arranged on the top surface side of the wiring board 3. The channel forming member 5 is constituted with a plate-shaped member made of, for example, polydimethylsiloxane (PDMS). In the position near to the rear of the channel forming member 5, hole portions 58 for positioning the channel forming member 5 are arranged at the position corresponding with the hole portions 33 arranged in the wiring board 3 such that the hole portions 58 pass through the channel forming member 5 in the thickness direction.

As illustrated in FIG. 4, a circular-shaped depressed portion 54 is provided so as to house the crystal resonator 4 in the inferior surface side of the channel forming member 5. In the front side of the depressed portion 54 in the inferior surface side of the channel forming member 5, grooves 253, 263, and 273 are formed to communicate with depressed portion 54, respectively, and to house each of wirings 25 to 27 formed in the wiring board 3. In the depressed portion 54, a surrounding portion 51 is arranged to partition and form a supply channel 57 for the sample solution with the front surface of the crystal resonator 4 when the channel forming member 5 is pressed to the wiring board 3 side. This surrounding portion 51 is constituted with an annular protrusion the outer edge of which is formed in an oval shape, such that the longitudinal direction of the surrounding portion 51 aligns with the front-rear direction of the sensing sensor 2. The surrounding portion 51 is constituted so as to protrude from the depressed portion 54 with a thickness of 300 μm, and the inside region of the surrounding portion 51 has a plane with height identical to the depressed portion 54. The channel forming member 5 includes through holes 52 and 53 that have openings at the front end and the rear end of the supply channel 57, respectively, and pass through the channel forming member 5 in the thickness direction. The supply channel 57 is constituted to gradually expand its width from the position of each of the through holes 52 and 53.

The first and the second vibrating regions 61 and 62 are laterally arranged alongside in the direction where supply liquid flows, and thus the supply liquid flows with respect to each of the first and second vibrating regions 61 and 62 simultaneously and similarly. Further, the element other than the load of the sensing object is constituted to be uniform as much as possible between each of the first and second vibrating regions 61 and 62, and thus the first and second vibrating regions 61 and 62 are constituted to serve as high-reliable reference.

As illustrated in FIG. 3 and FIG. 5, the through holes 52 and 53 removably includes an inlet-side capillary member 55 and an outlet-side capillary member 56 constituted with porous members, respectively. The inlet-side capillary member 55 is, for example, a column-shaped member and is constituted of, for example, a bundle of chemical fibers such as polyvinyl alcohol (PVA). The inlet-side capillary member 55 is arranged so as to plug the through hole 52. The upper end of the inlet-side capillary member 55 is arranged to be exposed in an injection port 23 formed in the upper-side cover body 21, which will be described later, and the lower end is arranged to enter the inside of the supply channel 57. The outlet-side capillary member 56 is also constituted of a bundle of chemical fibers such as polyvinyl alcohol (PVA). The outlet-side capillary member 56 is forming in an L shape that extends upward and then bends to horizontally extends rearward. The outlet-side capillary member 56 is arranged such that the outlet-side capillary member 56 plug the through hole 53 and its lower end enter the inside of the supply channel 57. Further the lower end of the outlet-side capillary member 56 inclines from the front side toward the rear side.

The other end side of the outlet-side capillary member 56 connects to one end side of an effluent channel 59 constituted of, for example, a hydrophilic glass tube. The other end side of the effluent channel 59 connects to an effluent absorbing portion 7 that is constituted with a capillary sheet 71 sucking, for example, fluid flowing out from the effluent channel 59 and an absorbing member 72 absorbing the fluid sucked by the capillary sheet 71. In the outside of the effluent absorbing portion 7, a case body 73 for prevention of leakage of liquid from the absorbing member 72 is arranged. In the drawings, reference numeral 75 denotes a supporting member that supports the effluent channel 59.

The upper-side cover body 21 is arranged such that the upper-side cover body 21 covers the wiring board 3 except the insertion portion 31, the channel forming member 5, and the effluent absorbing portion 7 from the upper side. The injection port 23 that inclines in a depressed cone shape is arranged on the top surface side of the upper-side cover body 21. As illustrated in FIG. 4, a pressing portion 90 for pressing the channel forming member 5 to the wiring board 3 is provided on the back surface side of the upper-side cover body 21. The pressing portion 90 is formed in, for example, a substantially box shape. The pressing portion 90 vertically and downward presses the whole top surface of the channel forming member 5 with its inferior surface when the upper-side cover body 21 fits with the lower-side case 22 and locks with one another. The pressing portion 90 includes a through hole 91 passing through into the injection port 23 at the position corresponding with the through hole 52.

A cutout 92 for ensuring an arrangement region for the effluent channel 59 and outlet-side capillary member 56 is formed from the position corresponding to the through hole 53 toward the rear side. The pressing portion 90 includes fixing pillars 93 for positioning the channel forming member 5 and the wiring board 3 by insertion of the fixing pillars 93 into the hole portions 58 and 33, which are arranged in the channel forming member 5 and the wiring board 3, respectively.

Figure 8:
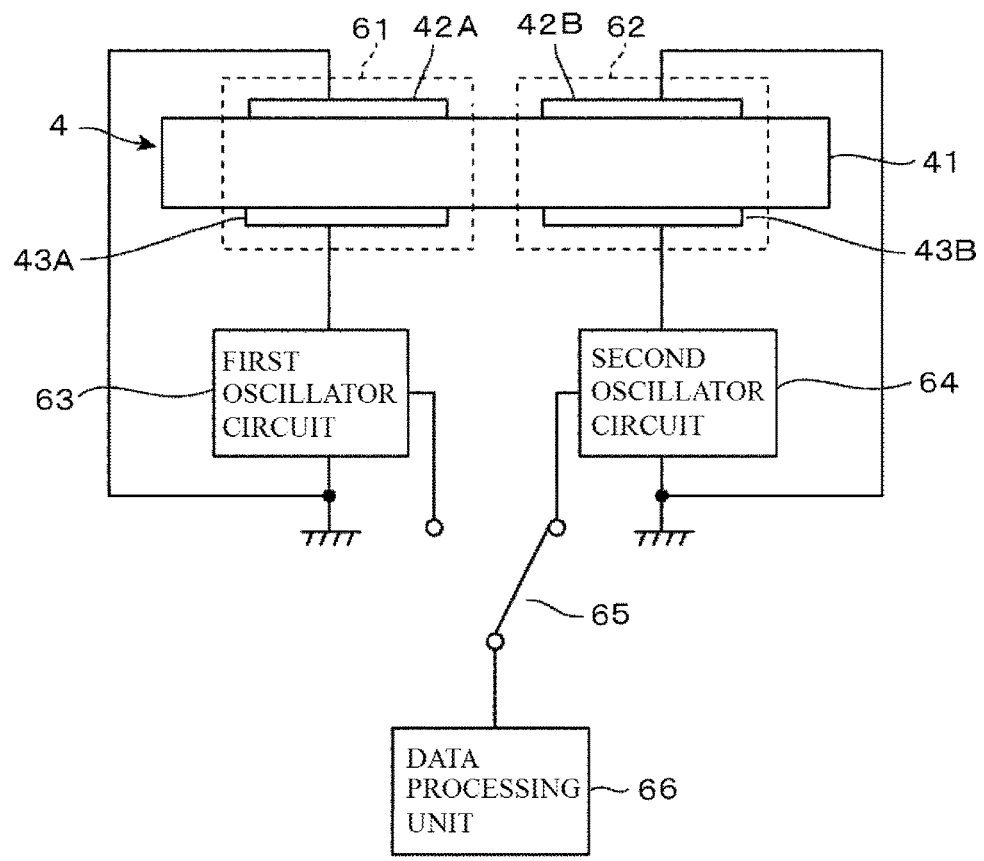
FIG. 8 is a schematic configuration diagram illustrating the configuration of the sensing device.

Subsequently, a description will be given of the whole configuration of the sensing device that uses the sensing sensor 2. Inserting the insertion portion 31 of the above-described sensing sensor 2 into the main body portion 12 electrically connects the terminal portions 252, 262, and 272 formed in the insertion portion 31 to connection terminal portions (not illustrated) formed in the main body portion 12 to correspond to the terminal portions 252, 262, and 272, and constitutes the sensing device. As illustrated in FIG. 8, a first oscillator circuit 63 and a second oscillator circuit 64 that are constituted, for example, with Colpitts circuit s are arranged in the main body portion 12. The first oscillator circuit 63 is constituted to oscillate the first vibrating region 61, which is the region sandwiched between the excitation electrode 42A and the excitation electrode 43A in the crystal resonator 4, and the second oscillator circuit 64 is constituted to oscillate the second vibrating region 62, which is the region sandwiched between the excitation electrode 42B and the excitation electrode 43B, respectively. The terminal portion 262 is connected so as to be ground potential in oscillation. The surfaces of the first vibrating region 61 and the second vibrating region 62 in the front surface side correspond to measurement regions.

The output sides of the first oscillator circuit 63 and the second oscillator circuit 64 are connected to a switch 65, and a data processing unit 66 is arranged in the latter part of the switch 65. The data processing unit 66 digitizes a frequency signal that is an input signal, and obtains time-series data of oscillation frequency "F1" outputted from the first oscillator circuit 63 and time-series data of oscillation frequency "F2" outputted from the second oscillator circuit 64.

The sensing device of this disclosure performs intermittent oscillation by alternately switching a channel 1 connecting the data processing unit 66 and the first oscillator circuit 63 and a channel 2 connecting the data processing unit 66 and the second oscillator circuit 64 by the switch 65. Consequently, the sensing device ensures avoiding interference between the two vibrating regions 61 and 62 of the sensing sensor 2 and obtaining the stable frequency signals. Subsequently, these frequency signals are, for example, time-shared and fed into the data processing unit 66. The data processing unit 66 calculates the frequency signals as, for example, digital values, and then performs arithmetic processing based on the time-shared data of the calculated digital values, and then displays the arithmetic operation result, for example, such as presence/absence of antigen on the display unit 16.

A description will be given of a method for determining presence/absence of the sensing object in the sample solution by the sensing device. First the sensing sensor 2 is connected to the main body portion 12, and a diluted liquid, which is composed of, for example, saline and includes no sensing object, is dropped in the injection port 23 by use of an injector (not illustrated). The liquid is absorbed to the inlet-side capillary member 55 by capillarity and flows inside the inlet-side capillary member 55, and then flows into the supply channel 57 to be supplied to the front-side surface of the crystal resonator 4.

Since the surface of the crystal element 41 constituting the crystal resonator 4 is hydrophilic, the liquid wets and expands inside the supply channel 57. Subsequently to the liquid expanding in the supply channel 57, the liquid in the inlet-side capillary member 55 is drawn out to the surface of the crystal element 41 by a surface tension, and thus the liquid continuously flows from the injection port 23 to the supply channel 57. The width of the supply channel 57 is constituted to radially expand toward the rear side and to become a constant width in a midstream region, and to gradually narrow toward the outlet-side capillary member 56 afterward. Since the excitation electrodes 42A and 42B are arranged alongside near the midstream of the supply channel 57, the liquid simultaneously flows on the surface of the excitation electrodes 42A and 42B at a constant speed.

Subsequently, when the liquid on the surface of the crystal resonator 4 reaches the outlet-side capillary member 56, the liquid is absorbed into the outlet-side capillary member 56 by capillarity and flows inside the outlet-side capillary member 56 to ooze out to the effluent channel 59. Here, due to workings of the principle of the siphon in addition to capillarity, the liquid that has been continuously and automatically supplied in a liquid receiving portion passes through the surface of the crystal resonator 4 to be discharged to the effluent channel 59.

The liquid inside the effluent channel 59 flows inside the effluent channel 59 to the downstream side and reaches the capillary sheet 71. When the liquid inside the effluent channel 59 reaches the capillary sheet 71, the liquid moves to the capillary sheet 71 side at a speed larger than the moving speed of the liquid that is flowing inside the effluent channel 59. When contacting the capillary sheet 71, the liquid expands and flows inside the capillary sheet 71 by capillarity to form a state where the liquid flow is discontinued inside the effluent channel 59.

When the liquid is separated inside the effluent channel 59, the liquid in the capillary sheet 71 side is absorbed into and retained in the absorbing member 72, which contacts with the capillary sheet 71. Meanwhile, since the liquid remaining in the injection port 23 attempts to flow toward the effluent channel 59 by capillarity and the principle of siphon, this liquid flow causes the liquid remaining in the effluent channel 59 to move to the downstream side and contact the capillary sheet 71 again. Consequently, when all the liquid in the liquid receiving portion flows out by repetition of separation of the liquid inside the effluent channel 59 and the liquid flow, the liquid movement in the effluent channel 59 halts in the state where the liquid is separated.

Subsequently, the sample solution with an amount identical to a buffer solution is supplied to the injection port 23. This increases pressure applied to the buffer solution absorbed in the inlet-side capillary member 55 and causes the buffer solution to flow toward the downstream side inside the effluent channel 59 again, and thus the sample solution is absorbed into the inlet-side capillary member 55. The absorbed sample solution flows into the supply channel 57 from the inlet-side capillary member 55 similarly to the buffer solution, and thus the buffer solution is replaced with the sample solution inside the supply channel 57.

Even in this case, since the excitation electrodes 42A and 42B are symmetrically formed when viewed from the inlet side to the outlet side of the supply channel 57, these excitation electrodes 42A and 42B equally receive a pressure variation by replacement of the liquid inside the supply channel 57. Thus, the oscillation frequencies of the first vibrating region 61 and the second vibrating region 62 by the pressure variation vary all together with one another. When the sample solution includes the sensing object, the adsorbing film 47 on the excitation electrode 42A adsorbs the sensing object. On the other hand, the sensing object is not adsorbed on the excitation electrode 42B. This decreases the frequency corresponding to the amount of adsorption of the sensing object to the adsorbing film 47 and varies F1-F2. Thus, this ensures determination of presence/absence of the sensing object based on the variation of F1-F2.

Here, a description will be given of adsorption of the sensing object to the adsorbing film 47. The sample solution, which is supplied to the supply channel 57, flows from the through hole 52 in the inlet side toward the downstream and first flows on the upper side of the extraction electrode 44. While the surface of Au electrode has a property to adsorb material contained in the sample solution, which is not limited to the sensing object, due to the formation of the blocking film 48 on the surface of the extraction electrode 44, the extraction electrode 44 does not adsorb the sensing object. Subsequently, the sample solution flows on the surface of the first and second vibrating regions 61 and 62 in the common electrode 42. In the first vibrating region 61, the blocking film 48 is formed in the region that is within 20% with respect to the length of the first vibrating region 61, from the upstream-side (the front-side) end portion. Consequently, the sensing object is not adsorbed in the region that is within 20% with respect to the length in the front-rear direction of the first vibrating region 61, from the upstream-side end portion, and the sensing object is adsorbed by the adsorbing film 47 formed in the downstream region with respect to the position that is 20% of the length in the front-rear direction of the first vibrating region 61, from the upstream-side end portion.

Figure 9:
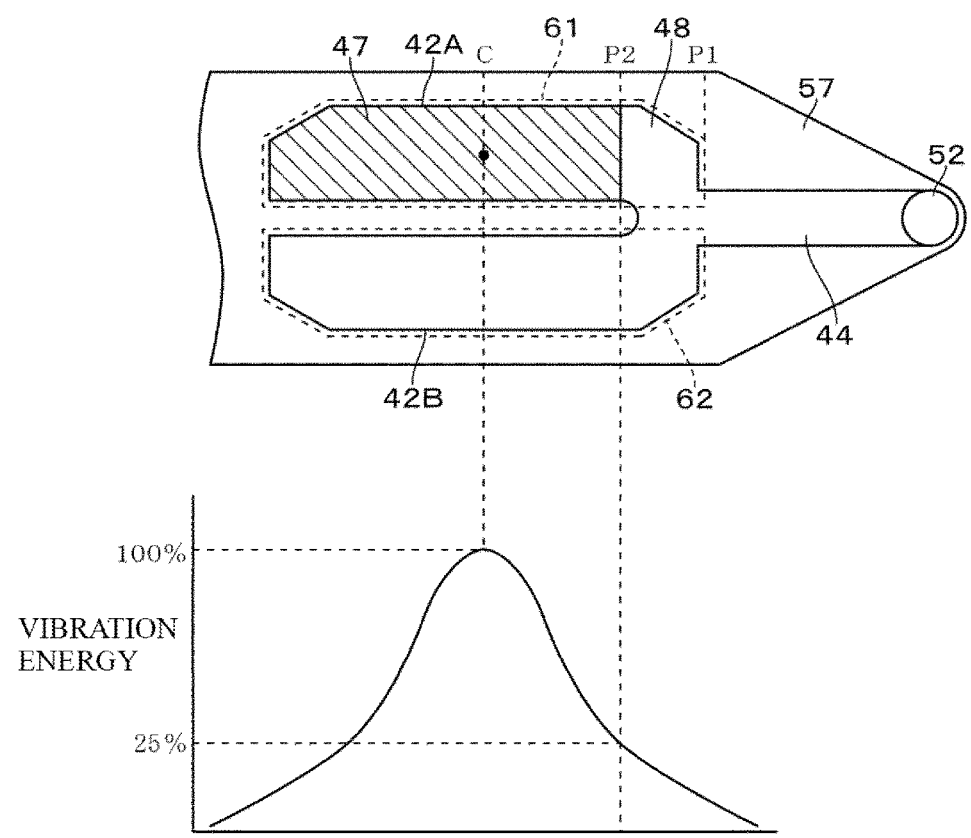
FIG. 9 is an explanatory drawing illustrating the distribution of the vibration energy of the crystal resonator.

Vibration in the vibrating region will be described. As illustrated in FIG. 9, when the first and second vibrating regions 61 and 62 vibrate, the central portion (vibration center) of each of the first and second vibrating regions 61 and 62 has larger amplitude and has larger energy generated by vibration, and the amplitude and the energy generated by vibration become smaller as the distance from the central portion of the vibrating region becomes larger. Consequently, adsorption of the sensing object at the portion nearer to the vibration center causes a larger energy variation and a larger frequency variation.

By viewing, for example, in the flow direction of the sample solution, at the position that has a distance of 30% of the length of the first and second vibrating regions 61 and 62, from the center of the first and second vibrating regions 61 and 62: the position that is 20% of the length of the first and second vibrating regions 61 and 62, from the upstream-side end portion, namely, at the boundary position between the adsorbing film 47 and the blocking film 48, the vibration energy decreases to approximately 25%. The larger the vibration energy is, the more the vibration energy decreases when the sensing object is adsorbed, and thus the larger the amount of frequency variation becomes.

When the sample solution containing the sensing object is supplied to the supply channel 57, and the sensing object is adsorbed by the adsorbing film 47, the sensing object is easily adsorbed in the upstream-side region of the supply channel 57, of the region with the adsorbing film 47 arranged. In contrast to this, since the sample solution, the concentration of the sensing object of which is diluted by the amount of the sensing object adsorbed in the upstream-side region, flows in the downstream-side region, the amount of adsorption of the sensing object decreases. In particular, in the sample solution with low concentration of the sensing object, when the sensing object is adsorbed in the upstream-side region, the sensing object is likely to be hardly adsorbed near the vibration center in the vibrating region.

Figure 10:
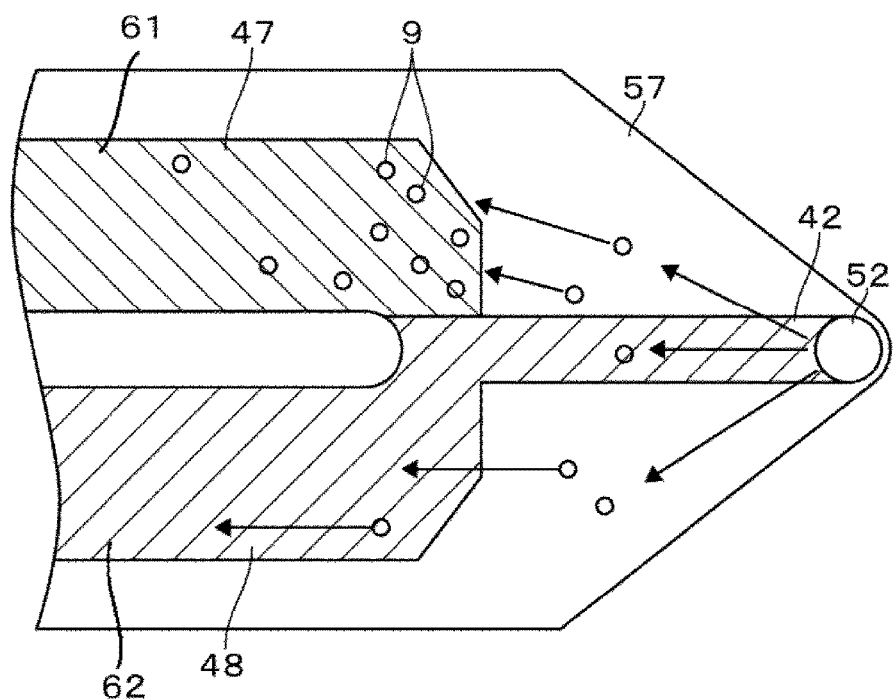
FIG. 10 is an explanatory drawing illustrating adsorption of sensing objects in a conventional crystal resonator.
Figure 11:
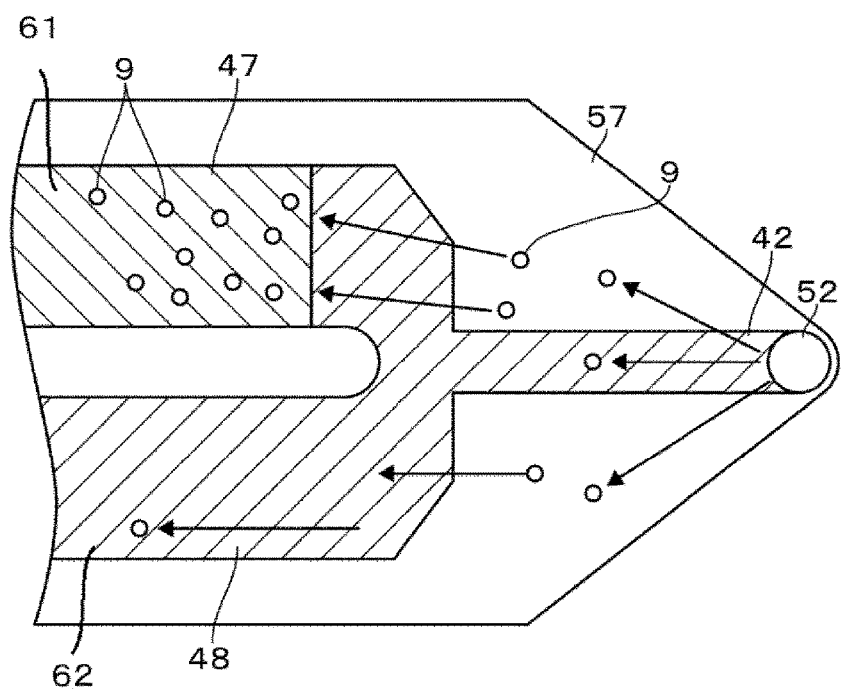
FIG. 11 is an explanatory drawing illustrating the adsorption of the sensing object in the crystal resonator according to an embodiment disclosed here.

As illustrated in FIG. 10, forming the adsorbing film 47 up to the upstream-side end portion of the first vibrating region 61 causes the region with small vibration energy in the first vibrating region 61 adsorb many sensing objects 9, and thus decreases the adsorption amount of the sensing object 9 in the portion near the center of the first vibrating region 61, which has large vibration energy. In contrast to this, as illustrated in FIG. 11, in the above-described embodiment, the blocking film 48 is formed in the region with small vibration energy in the first vibrating region 61 in the upstream side of the supply channel 57, which is, in this example, the region where the vibration energy is equal to or less than 30% of the vibration energy in the central portion of the first vibrating region 61. This ensures that the sensing object 9 is adsorbed in the region with large vibration energy, which is the position near the center in the first vibrating region 61.

In the above-described embodiment, in the sensing sensor 2, which causes the adsorbing film to adsorb the sensing object in the sample solution to sense the sensing object by flowing the sample solution from the front side to the rear side of the one surface side of the crystal resonator 4, the front-side end portion of the adsorbing film 47 in the flow of the sample solution is arranged at the position that has a length of 20% with respect to the length of the first vibrating region 61, from the front-side end portion of the first vibrating region 61. The blocking film 48 is arranged in the region where the adsorbing film 47 is not arranged, on the one surface side of the crystal resonator 4. Consequently, this ensures to cause the sensing object 9 contained in the sample solution to be adsorbed in the region with large vibration energy in the first vibrating region 61, and thus to improve accuracy of the sensing sensor 2 even for a low concentration sample solution. In this case, this effect is obtained by arranging the upstream-side end portion of the adsorbing film 47 in the region expressed as follows: assuming that the upstream-side end portion of the vibrating region is P1, the upstream-side end portion of the adsorbing film is P2, and the central portion of the vibrating region is C, (the distance L0 from C to P1)×0.4≤(the distance L2 from P1 to P2)≤(the distance L0 from C to P1)×0.8.

Figure 12:
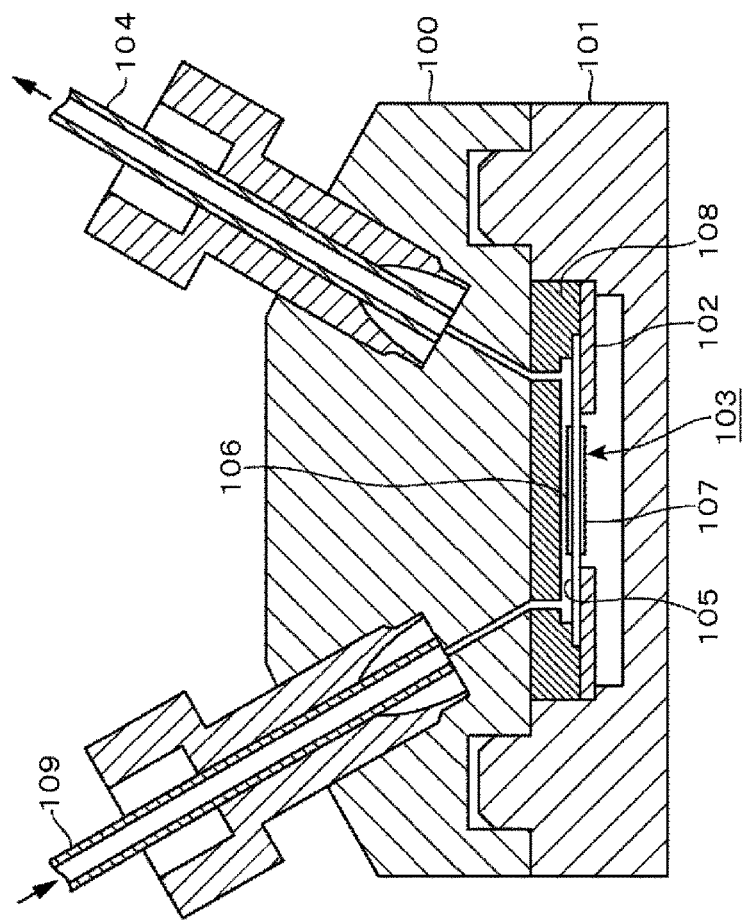
FIG. 12 is a longitudinal cross-sectional view illustrating other example of the embodiment disclosed here.

The sensing device of this disclosure is not limited to a sensing device that uses a sensing sensor supplying the crystal resonator 4 with a sample solution with use of capillarity, and a sensing device using a flow-type sensing sensor that flows a sample solution may be employed. FIG. 12 illustrates such sensing device. In FIG. 12, reference numeral 100 denotes an upper member, reference numeral 101 denotes a lower member, reference numeral 102 denotes a wiring board, reference numeral 103 denotes a crystal resonator, reference numeral 105 denotes a crystal element, reference numerals 106 and 107 denote electrodes, reference numeral 108 denotes a pressing member, reference numeral 109 denotes a liquid supply port, and reference numeral 104 denotes a liquid discharge port. The upper member 100 is constituted to be separable with respect to the lower member 101, and thus the crystal resonator 103 is replaceable. The flow-type measuring unit causes a sample solution to flow from the liquid supply port 109 to the liquid discharge port 104 side via the space on the front surface side of the crystal resonator 103, and measures the oscillation frequency of the crystal resonator 103 with a reference solution or the sample solution flowing. This disclosure is applicable in using such sensing device.

The inventor considers that the position P2 of the front-side end portion of the adsorbing film 47 for ensuring the effect of obtaining high detection sensitivity is located in the range where the vibration energy is from 25% to 80% with respect to the vibration energy (the largest vibration energy in the front-rear direction of the vibrating region) of the central portion in the front-rear direction of the vibrating region. When the vibration energy at the position P2 of the front-side end portion of the adsorbing film 47 is equal to or less than 25% of the largest vibration energy, the sensing object is more adsorbed in the region with low vibration energy, and thus the detection sensitivity lowers. When the vibration energy at the position P2 exceeds 80% of the largest vibration energy, in view of the premise of downsizing of the sensing sensor 2, the area of the adsorbing film 47 becomes narrow and the detection sensitivity lowers.

In terms of visualizing such a technical idea and clarifying the scope of this disclosure, the position P2 of the front-side end portion of the adsorbing film is settable as follows: (the distance L0 from C to P1)×0.4≤(the distance L2 from P1 to P2)≤(the distance L0 from C to P1)×0.8. For example, the position P2 is set to be the position expressed as follows: (the distance L0 from C to P1)×0.4=(the distance L2 from P1 to P2).

Working Example

The following test was performed for verifying the effect of the embodiment disclosed here. The working example employed the example that used the sensing sensor indicated in the above-described embodiment. Further, a comparative example was performed. The comparative example employed the following example: the example had a configuration identical to the working example except that slits of a rubber plate were formed in sizes facing the whole surfaces of the vibrating regions, and an adsorbing film was formed on the whole surface of the first vibrating region. By using three sensing sensors for each of the working example and the comparative example, measurement for low-concentration CRP (10 ng/ml) was performed, and the amount of frequency variation was examined.

Figure 13:
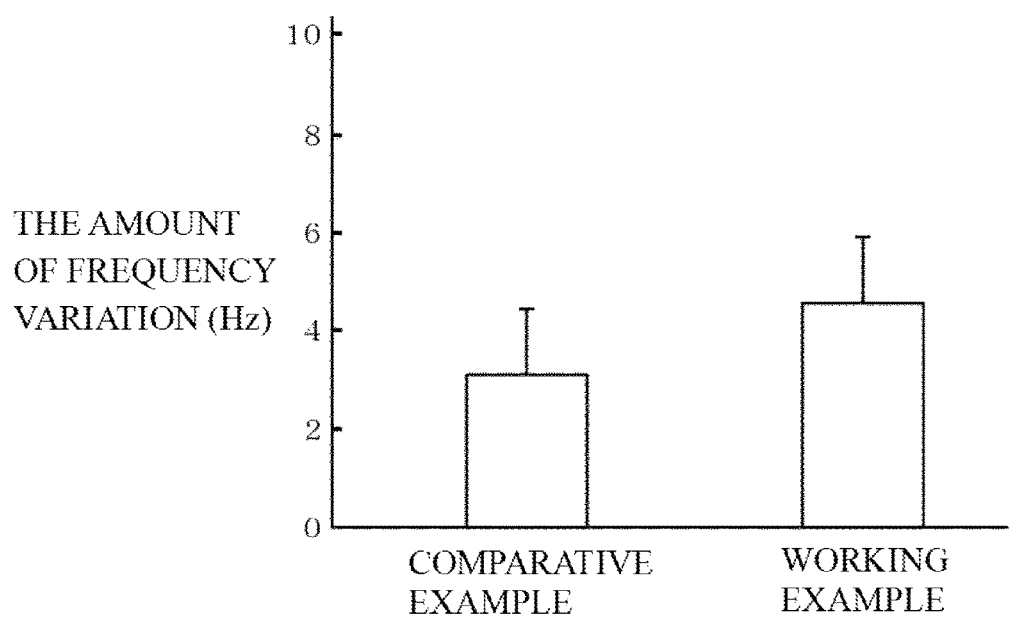
FIG. 13 is a characteristic diagram illustrating frequency variations in a working example and a comparative example.

FIG. 13, which illustrates the results, is a characteristic diagram that indicates the average values of the frequency-variation values detected when the measurement was performed using each sensing sensor according to the comparative example and the working example.

According to this result, while the comparative example detected an amount of frequency variation of approximately 3 Hz, the working example detected the amount of frequency variation of approximately 4.8 Hz. Thus, the working example detected 1.6 times frequency variation compared to the comparative example.

Therefore, using the sensing sensor 2 described here ensures enhancing the detection sensitivity.

In this disclosure, the sensing sensor, which causes the adsorbing film to adsorb the sensing object in the sample solution by flowing the sample solution from one end side of the one surface side of the crystal resonator toward the other end side, includes the first and second vibrating regions with the excitation electrodes arranged on the one surface side and the other surface side of the crystal element. Further, in arranging the adsorbing film, which adsorbs the sensing object in the sample solution, in one vibrating region, the adsorbing film is arranged such that the adsorbing film is located in the region that includes the central portion in the front-rear direction of the one vibrating region and where, assuming that the front end portion of the vibrating region is P1, the front end portion of the adsorbing film is P2, the central portion of the vibrating region is C, the front end portion of the adsorbing film P2 satisfies a relational expression expressed as follows: (a distance from C to P1)×0.4≤(a distance from P1 to P2)≤(a distance from C to P1)×0.8. The blocking layer, which blocks adsorption of the sensing object, is arranged in the other region of the excitation electrode on the one surface side. This ensures that the sensing object is surely adsorbed in the region with large vibration energy in the vibrating region when the sample solution is supplied, and thus ensures improving detection sensitivity.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sensing sensor, comprising:
   a common crystal element, having a first vibrating region and a second vibrating region that are constituted with respective excitation electrodes arranged on one surface side and another surface side of the common crystal element, the first vibrating region and the second vibrating region being laterally separated with one another;
   an adsorbing film formed on a surface of the excitation electrode in the one surface side corresponding to one vibrating region of the first vibrating region and the second vibrating region, the adsorbing film adsorbing a sensing object in a sample solution;
   a blocking layer arranged over a whole region other than a region where the adsorbing film is formed on the excitation electrode in the one surface side, the blocking layer blocking adsorption of the sensing object in the sample solution;
   a wiring board including a connection terminal portion to connect the excitation electrode to a frequency measuring unit, the common crystal element being fixed to the wiring board such that the common crystal element forms a space in the another surface side of the first vibrating region and the second vibrating region; and
   a channel forming member arranged to cover a region of the one surface side of the wiring board to form a channel that causes the sample solution to flow from a front end side toward a rear end side with the region, the region of the one surface side of the wiring board including the first vibrating region and the second vibrating region in the one surface side of the common crystal element, the channel including an injection port for injecting the sample solution in a front end side of the channel and a discharge port for discharging the sample solution from a rear end side of the channel, wherein the adsorbing film is arranged such that the adsorbing film is located in a region including a central portion in a front-rear direction of the one vibrating region, and assuming that a front end portion of the vibrating region is P1, the front end portion of the adsorbing film is P2, and the central portion of the vibrating region is C, the front end portion of the adsorbing film P2 satisfies a relational expression expressed as follows:

(a distance from $C$ to $P1$)×0.4≤(a distance from $P1$ to $P2$)≤(a distance from $C$ to $P1$)×0.8.

2. The sensing sensor according to claim 1, wherein the common crystal element is constituted of AT-cut.

3. The sensing sensor according to claim 1, wherein the excitation electrodes are made of gold.

4. The sensing sensor according to claim 1, wherein the adsorbing film is constituted with antibody selectively combining with the sensing object.

5. The sensing sensor according to claim 1, wherein the blocking layer is constituted of bovine serum albumin or skim milk.

6. The sensing sensor according to claim 1, wherein the wiring board includes three wirings extending in a longitudinal direction on a front surface side of the wiring board.

7. The sensing sensor according to claim 1, wherein the channel forming member is constituted with a plate-shaped member made of polydimethylsiloxane.

* * * * *